United States Patent [19]
Hardtmann

[11] 3,975,386
[45] Aug. 17, 1976

[54] N-SUBSTITUTED-3-AZAISATOIC ANHYDRIDES

[75] Inventor: Goetz E. Hardtmann, Florham Park, N.J.

[73] Assignee: Sandoz, Inc., E. Hanover, N.J.

[22] Filed: Jan. 3, 1975

[21] Appl. No.: 538,407

Related U.S. Application Data

[63] Continuation-in-part of Ser. No. 326,850, Jan. 26, 1973, Pat. No. 3,859,289.

[52] U.S. Cl............................................. 260/244 A
[51] Int. Cl.² .............. C07D 265/00; C07D 273/00; C07D 295/00
[58] Field of Search .............................. 260/244 A

[56] References Cited
UNITED STATES PATENTS
3,598,823   8/1971   Hardtman ........................ 260/256.4

*Primary Examiner*—Sam Rosen
*Assistant Examiner*—D. W. Robinson
*Attorney, Agent, or Firm*—Gerald D. Sharkin; Richard E. Vila

[57] ABSTRACT

The novel 3,4-dihydro-1,3 dioxo-1,4 pyrido-(2,3-d)(1,3) oxazine compounds of this invention are useful as intermediates in the preparation of pharmaceutically active pyridopyrimidine-one compounds.

22 Claims, No Drawings

N-SUBSTITUTED-3-AZAISATOIC ANHYDRIDES

This application is a continuation-in-part of application Ser. No. 326,850, filed Jan. 26, 1973 and now U.S. Pat. No. 3,859,289.

The present invention relates to heterocyclic substituted tricyclic compounds which are pyrimidinones, to their preparation and to valuable intermediates useful in such preparations. The invention also relates to pharmaceutical methods and compositions for utilization of the tricyclic compounds based on their biological activity.

The compounds of the invention may be represented by the structural formula I:

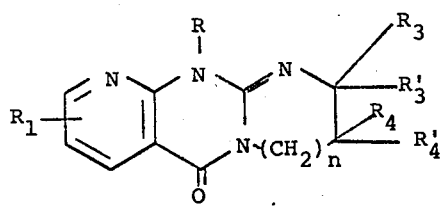

wherein R is alkyl of 1 to 7 carbon atoms, alkenyl of 3 to 8 carbon atoms, alkynyl of 3 to 6 carbon atoms, cyanoalkyl of 2 to 6 carbon atoms,

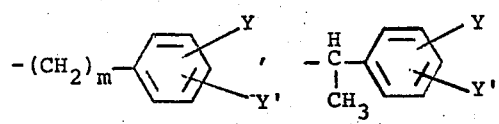

or

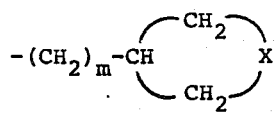

$m$ is 0 to 2, $R_1$ is hydrogen, alkyl of 1 to 4 carbon atoms or alkoxy of 1 to 3 carbon atoms, $n$ is 0 to 2, X is a direct bond or $-(CH_2)_p-$, $p$ is 1 to 3, each of Y and Y' is, independently, hydrogen, halo of atomic weight not greater then 36, i.e., fluoro or chloro, or lower alkyl of 1 to 3 carbon atoms, or both are lower alkoxy of 1 to 2 carbon atoms, or one is hydrogen and the other bromo, trifluoromethyl or lower alkoxy of 1 to 2 carbon atoms, and each of $R_3$, $R_3'$, $R_4$ and $R_4'$ is hydrogen or alkyl of 1 to 3 carbon atoms provided that no more than 3 of $R_3$, $R_3'$, $R_4$ and $R_4'$ are alkyl or a pharmaceutically acceptable acid addition salt thereof.

The compounds of the formula I may be prepared by a reaction in a Step A of a compound of the formula II:

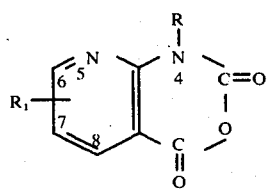

wherein R and $R_1$ are as defined with a compound of formula III:

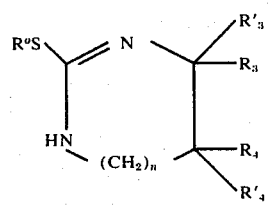

wherein $n$, $R_3$, $R_3'$, $R_4$ and $R_4'$ are as defined and $R°$ is lower alkyl or benzyl.

The preparation of compounds I by the reaction of Step A can be carried out at temperature in the range of 20°C. to 160°C., more usually 20°C. to 140°C., preferably 80°C. to 120°C. The reaction is conveniently carried out in an organic solvent of conventional type providing an inert reaction medium. Cyclic ethers and aromatic solvents suitable for use at reflux temperatures represent the preferred solvents, particularly dioxane and toluene. The reaction is preferably carried out in the presence of a base, e.g., sodium hydroxide or sodium carbonate; and if the compound III is employed directly in acid addition salt form then it is desirable to employ an amount of base somewhat greater than the amount necessary to neutralize the acid. In general, the reaction product of formula I may be recovered from the reaction of Step A by working up by conventional procedures.

The compounds of the formula II are novel and may be prepared by reacting a compound of the formula IV:

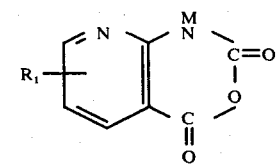

in which $R_1$ is as defined and M is hydrogen or an alkali metal, with a compound of the formula V:

$$RX°$$   V in which R is as defined and X° is halo, e.g., chloro or bromo.

The preparation of compounds II from compounds IV and V may be carried out at temperatures of from 0°C. to 100°C., preferably 20°C. to 50°C. The reaction is conveniently effected in an inert organic solvent which may be of conventional type, e.g., dimethylacetamide. The reaction is preferably effected with a compound IV in which M is an alkali metal and such compounds are prepared in a conventional manner by reacting a compound in which M is hydrogen with a strong base such as an alkali metal hydride, e.g., sodium hydride. If the compound IV in which M is hydrogen is employed the reaction is carried out in the presence of a strong base, e.g., an alkali metal alkoxide or hydroxide.

The compounds of formulae III, IV and V are either known or may be prepared from known materials by established procedures. With respect to the compounds of the formula IV (M being hydrogen) reference may be made to U.S. Pat. No. 3,622,573 and Beckwith et al., J. Chem. Soc. (C), 1968, 2756.

The preferred bronchodilator compounds of the invention are those having one or more of the following significances: (1) R being benzyl or substituted benzyl, particularly p-halobenzyl; (2) $R_1$ equals hydrogen; and (3) $n$ equals 0.

Also within the scope of the compounds of formula I of the invention are pharmaceutically acceptable salts not materially depreciating the pharmacological effect of the compounds. Such salts include the acid addition salts of known type, e.g., the hydrochloride, maleate and the like. The acid addition salts may be produced from the corresponding free bases by conventional procedures. Conversely, the free bases may be obtained from the salts by procedures known in the art.

The compounds of formula I of the invention are useful because they possess biological activity. In particular, the compounds of the formula I in which R is alkyl, alkenyl, alkynyl, cyanoalkyl or substituted or unsubstituted benzyl, phenethyl or α-methyl-benzyl are useful as bronchodilator agents as indicated by measuring bronchial resistance on intravenous administration (0.2 – 5 mgs./kgs.) in the anesthetized guinea pig and according to the test of Knozett and Rossler, Arch. Exp. Path. and Pharmak. 195:71 (1940); and by observing the respiratory status on oral administration (0.5 – 100 mgs./kgs.) to the unanesthetized guinea pig exposed to aerosolized histamine dihydrochloride according to a modification of the method of Van Arman et al., J. Pharm. Pharmacol. Exptl. Therap. 133:90–97, 1961; and in vitro by observing the effect (0.1 – 30 micrograms/ml.) on strips of guinea pig trachea according to the method of Constantine, J. Pharm. Pharmacol. 17: 384–385, 1960. For such use and depending upon known variables satisfactory results are obtained in general on the daily administration of from 0.6 to 100 milligrams per kilogram of body weight, preferably given in divided doses 2 to 4 times a day, or in sustained release form. For most mammals the administration of from 60 to 1500 milligrams per day provides satisfactory results and dosage forms suitable for internal administration comprise 15 to 750 milligrams of the compound in admixture with a solid or liquid pharmaceutical carrier or diluent.

The compounds of formula I in which R is alkyl, cycloalkyl, cycloalkylalkyl or substituted or unsubstituted phenyl are also useful as hypotensive agents as indicated by a lowering of blood pressure on intravenous administration (2–30 mg./kg.) to the anesthetized dog. For such use and depending upon known variables satisfactory results are obtained in general on daily administration of from 2 to 100 milligrams per kilogram of body weight. For most mammals the administration of from 40 to 1000 milligrams per day provides satisfactory results and dosage forms for internal administration comprise from 10 to 500 milligrams in combination with a suitable carrier.

The compounds of the formula I in which R is alkyl, alkenyl, alkynyl or cyanoalkyl are also useful as antiinflammatory agents as indicated by an inhibition of Carrageenan induced edema in rats on oral administration (15–150 mg./kg.). For such use, the compounds may be combined with a pharmaceutically acceptable carrier, and such other conventional adjuvants as may be necessary, and administered orally in such forms as tablets, capsules, elixirs, suspensions and the like or parenterally in the form of an injectable solution or suspension. The dosage administered will, of course, vary depending upon the compound used and the mode of administration. However, in general, satisfactory results are obtained when administered at a daily dosage of from about 3 milligrams to about 180 milligrams per kilogram of body weight, preferably given in divided doses 2 to 4 times a day, or in sustained release form. For most mammals the administration of from about 200 milligrams to about 2000 milligrams of the compound per day provides satisfactory results and dosage forms suitable for internal administration comprise from about 50 milligrams to about 1000 milligrams of the compound in admixture with a solid or liquid pharmaceutical carrier or diluent.

For the uses indicated above, the compounds may be combined with a pharmaceutically acceptable carrier, and such other conventional adjuvants as may be necessary, and administered orally or parenterally. For most uses, oral administration with carriers is preferred and may take place in such conventional forms as tablets, dispersible powders, granules, capsules, suspensions, syrups and elixirs. Such compositions may be prepared according to any method known in the art for the manufacture of pharmaceutical compositions, and such compositions may contain one or more conventional adjuvants, such as sweentening agents, flavoring agents, coloring agents and preserving agents, in order to provide an elegant and palatable preparation. Tablets may contain the active ingredient in admixture with conventional pharmaceutical excipients, e.g., inert diluents such as calcium phosphate, calcium sulphate dihydrate, lactose and talc, granulating and disintegrating agents, e.g., starch and alginic acid, polyvinyl pyrrolidone and acacia, and lubricating agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert solid diluent, e.g., calcium carbonate, calcium phosphate and kaolin. The preferred pharmaceutical compositions from the standpoint of preparation and ease of oral administration are solid compositions, particularly hard-filled capsules and tablets. Parenteral administration may be in such conventional forms as injectionable solutions and suspensions.

A representative formulation is a tablet for oral administration 2 to 4 times a day for prophylactic treatment of bronchial asthma and prepared by conventional tabletting techniques to contain the following ingredients:

| Ingredients | Weight (mg.) |
| --- | --- |
| 10-(4'-fluorobenzyl)-2,3-dihydro-imidazo [1,2-a]pyrido[2,c-d]pyrimidine-5(10H)-one | 50 |
| Tragacanth | 10 |
| Lactose | 222.5 |
| Corn Starch | 25 |
| Talcum | 15 |
| Magnesium Stearate | 2.5 |

A representative formulation is also a capsule for oral administration 2 to 4 times a day for prophylactic treatment of bronchial asthma and prepared by conventional capsulating techniques to contain the following ingredients:

| Capsule Ingredients | Weight (mg.) |
| --- | --- |
| 10-(4'-fluorobenzyl)-2,3-dihydro-imidazo [1,2-a]pyrido[2,3-d]pyrimidine-5(10H)-one | 50 |
| Lactose | 316 |
| Sterotex K (a triglycerol ester lubricant) | 10 |

In addition the compounds of the formula I which are useful as bronchodilators may be administered for such use by inhalation therapy in a conventional manner, e.g., by the use of nebulizers, vaporizers, aerosols and the like. Compositions for use in administration by inhalation therepy may be prepared according to conventional procedures and contain the usual conventional ingredients employed in such compositions. A representative aerosol formulation prepared by conventional technique for use with a metered value system contains the following ingredients:

| | |
| --- | --- |
| 10-(4'-fluorobenzyl)-2,3-dihydro-imidazo [1,2-a]pyrido[2,3-d]pyrimidine-5(10H)-one | 0.4 – 20% |
| Ethyl alcohol | 10 – 40% |
| Ascorbic acid | 1 – 10% |
| Freon 11 | 10 – 30% |
| Freon 114 | 10 – 30% |
| Freon 12 | 30 – 60% |
| Buffer System - pH control | q.s. |
| Flavor | q.s. |

A representative formulation is also a capsule for oral administration 2 to 4 times a day for reducing blood pressure, e.g., treating hypertension, and prepared by conventional capsulating techniques to contain the following ingredients:

| Capsule Ingredients | Weight (mg.) |
| --- | --- |
| 10-cyclopropylmethyl-2,3-dihydro-imidazo [1,2-a]pyrido[2,3-d]pyrimidine-5(10H)-one | 50 |
| Lactose | 300 |

Capsules prepared by conventional capsulating techniques and containing 200 milligrams of finely divided lactose and 100–150 milligrams of a compound of Examples 1, 3n, 3z-7, 3z-8 or 3z-9 may be used in the treatment of inflammation on the administration of one such capsule four times a day.

The following examples show representative compounds encompassed within the scope of this invention and the manner in which such compounds are prepared. However, it is to be understood that the examples are for purposes of illustration only.

EXAMPLE 1

10-Methyl-2,3-dihydro-imidazo[1,2-a]pyrido[2,3-d]pyrimidine-5 (10H)-one.

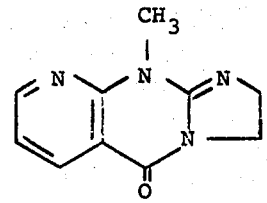

STEP A: To a solution of 7.5 g. of 3,4-dihydro-1,3-dioxo1H-pyrido[2,3-d][1,3]oxazine in 200 ml. of dimethylacetamide is added portionwise 2.3 g. of sodium hydride and the resulting mixture stirred at room temperature for 45 minutes. There is then added 7.0 g. of methyl iodide and the mixture stirred at room temperature for an additional 30 minutes. The resulting mixture is poured onto ice/water, extracted twice with ethyl acetate and the combined extracts washed 4 times with water, dried and evaporated to a solid which is dissolved in methylene chloride. The solution is treated by addition of diethyl ether on a steam bath to crystalline 4-methyl-3,4-dihydro-1,3-dioxo-1H-pyrido [2,3-d][1,3]oxazine, m.p. 167°–169°C.

STEP B: A mixture of 15.4 g. of 4-methyl-3,4-dihydro-1,3-dioxo-1H-pyrido [2,3-d][1,3]oxazine, 12.0 g. of 2-methylmercaptoimidazoline, 2 pellets of sodium hydroxide and 250 ml. of dioxane is refluxed for 2 hours. The reaction mixture is then evaporated to dryness, the residue dissolved in methylene chloride, washed with water, extracted twice with 2N hydrochloride acid solution, the combined extracts washed with methylene chloride and then made basic with ice/2N sodium hydroxide solution. Adding of seeding crystals results in a precipitate which is recovered by filtering, washed 4 times with water, dried in high vacuum, redissolved in methylene chloride and ethanol added on a steam bath to obtain 10-methyl-2,3-dihydro-imidazo[1,2-a]pyrido[2,3-d]pyrimidine-5(10H)-one, m.p. 168°–171°C.

EXAMPLE A

Following the procedures of Step A of Example 1 the following additional compounds of the formula II are prepared:

| Example | R | $R_1$ |
| --- | --- | --- |
| A-1 | p-fluorobenzyl | H |
| A-2 | benzyl | H |
| A-3 | cyclopropylmethyl | H |
| A-4 | ethyl | H |
| A-5 | hexyl | H |
| A-6 | o-methylbenzyl | H |
| A-7 | cyclohexyl | H |
| A-8 | p-chlorobenzyl | H |
| A-9 | p-bromobenzyl | H |
| A-10 | m,p-difluorobenzyl | H |
| A-11 | phenyl | H |
| A-12 | m-trifluoromethylbenzyl | H |
| A-13 | m,p-dimethoxyphenyl | H |
| A-14 | α-methylbenzyl | H |
| A-15 | 5-hexenyl | H |
| A-16 | 2-butenyl | H |
| A-17 | p-fluorobenzyl | 7-methyl |
| A-18 | p-fluorobenzyl | 6-methoxy |
| A-19 | p-fluorobenzyl | 6-methyl |

| Example | R | R₁ |
|---------|---|----|
| A-20 | propargyl | H |
| A-21 | 2-butynyl | H |
| A-22 | cyanomethyl | H |

EXAMPLE 2

10-(4'-fluorobenzyl)-2,3-dihydro-imidazo[1,2-a]pyrido[2,3-d]pyrimidine-5(10H)-one.

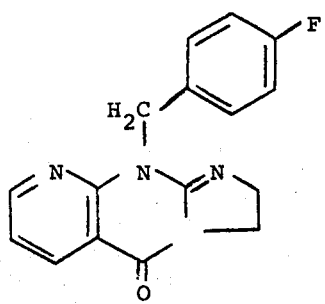

A mixture of 14.2 g. of 4-(4'-fluorobenzyl)-3,4-dihydro-1,3-dioxo-1H-pyrido[2,3-d][1,3]oxazine, 6.8 g. of 2-methylmercapto-imidazoline, 350 ml. of dioxane and 2 pellets of sodium hydroxide is refluxed for 8 hours and evaporated to dryness. The residue is dissolved in methylene chloride, washed with water, extracted twice with 2N hydrochloric acid and the combined acid extracts washed with methylene chloride followed by treatment with charcoal and filtered. The filtrate is then made basic with ice/2N sodium hydroxide, seeding crystals added and the resulting crystalline material is washed 3 times with water, air dried, washed twice with diethyl ether, dried under high vacuum and recrystallized from methylene chloride/diether ether (1:1). The resulting crystalline materials are dissolved in chloroform and ethanol added while heating on a steam bath to obtain 10-(4'-fluorobenzyl)-2,3-dihydro-imidazo[1,2-a]pyrido[2,3-d]pyrimidine-5(10H0-one, m.p. 202°–205°C.

EXAMPLE 3

Following essentially the procedures of Examples 1 and 2 the following additional compounds of the invention are prepared:

a. 10-benzyl-2,3-dihydro-imidazo[1,2-a]pyrido[2,3-d]pyrimidine-5(10H)-one.
b. 10-cyclopropylmethyl-2,3-dihydro-imidazo[1,2-a]pyrido[2,3-d]pyrimidine-5(10H)-one, m.p. 139-142°C.
c. 10-ethyl-2,3-dihydro-imidazo[1,2-a]pyrido[2,3-d]pyrimidine-5(10H)-one.
d. 10-hexyl-2,3-dihydro-imidazo[1,2-a]pyrido[2,3-d]pyrimidine-5(10H)-one.
e. 10-(2'-methylbenzyl)-2,3-dihydro-imidazo[1,2-a]pyrido[2,3-d]pyrimidine-5(10H)-one.
f. 10-cyclohexyl-2,3-dihydro-imidazo[1,2-a]pyrido[2,3-d]pyrimidine-5(10H)-one.
g. 10-(4'-chlorobenzyl)-2,3-dihydro-imidazo[1,2-a]pyrido[2,3-d]pyrimidine-5(10H)-one.
h. 10-(4'-bromobenzyl)-2,3-dihydro-imidazo[1,2-a]pyrido[2,3-d]pyrimidine-5(10H)-one.
i. 10-(3',4'-difluorobenzyl)-2,3-dihydro-imidazo[1,2-a]pyrido[2,3-d]pyrimidine-5(10H)-one.
j. 10-phenyl-2,3-dihydro-imidazo[1,2-a]pyrido[2,3-d]pyrimidine-5(10H)-one.
k. 10-(3'-trifluoromethylbenzyl)-2,3-dihydro-imidazo[1,2-a]pyrido[2,3-d]pyrimidine-5(10H)-one.
l. 10-(3,4-dimethoxybenzyl)-2,3-dihydro-imidazo[1,2-a]pyrido[2,3-d]pyrimidine-5(10H)-one.
m. 10-(α-methylbenzyl)-2,3-dihydro-imidazo[1,2-a]pyrido[2,3-d]pyrimidine-5(10H)-one.
n. 10-(5-hexenyl)-2,3-dihydro-imidazo[1,2-a]pyrido[2,3-d]pyrimidine-5(10H)-one.
o. 10-(2-butenyl)-2,3-dihydro-imidazo[1,2-a]pyrido[2,3-d]pyrimidine-5(10H)-one.
p. 10-(4'-fluorobenzyl)-7-methyl-2,3-dihydro-imidazo[1,2-a]pyrido[2,3-d]pyrimidine-5(10H)-one.
q. 10-(4'-fluorobenzyl)-8-methoxy-2,3-dihydro-imidazo[1,2-a]pyrido[2,3-d]pyrimidine-5(10H)-one.
r. 10-(4'-fluorobenzyl)-2,2-dimethyl-2,3-dihydro-imidazo[1,2-a]pyrido[2,3-d]pyrimidine-5(10H)-one.
s. 10-(4'-fluorobenzyl)-2-methyl-2,3-dihydro-imidazo[1,2-a]pyrido[2,3
t. pyrimidine-5(10H)-one. t. 10-(4'-fluorobenzyl)-2,3-dimethyl-2,3-dihydro-imidazo[1,2-a]pyrido[2,3-d]pyrimidine-5(10H)-one.
u. 11-(4'-fluorobenzyl)-1,2,3,4-tetrahydro-2H-pyrido[2,3-d]pyrimido[1,2-a]pyrimidine-6-one.
v. 11-benzyl-1,2,3,4-tetrahydro-2H-pyrido[2,3-d]pyrimido[1,2-a]pyrimidine-6-one.
w. 11-cyclopropylmethyl-1,2,3,4-tetrahydro-2H-pyrido[2,3-d]pyrimido[1,2-a]pyrimidine-6-one.
x. 11-(4-fluorobenzyl)-3-methyl-3-ethyl-1,2,3,4-tetrahydro-2H-pyrido[2,3-d]pyrimido[1,2-a]pyrimidine-6-one.
y. 11-phenyl-1,2,3,4-tetrahydro-2H-pyrido[2,3-d]pyrimido[1,2-a]pyrimidine-6-one.
z. 11-methyl-1,2,3,4-tetrahydro-2H-pyrido[2,3-d]pyrimido[1,2-a]pyrimidine-6-one.
z-1. 11-(5-hexenyl)-1,2,3,4-tetrahydro-2H-pyrido[2,3-d]pyrimido[1,2-a]pyrimidine-6-one.
z-2. 10-(4'-fluorobenzyl)-8-methyl-2,3-dihydroimidazo[1,2-a]pyrido[2,3-d]pyrimidine-5(10H)-one.
z-3. 12-(4'-fluorobenzyl)-2,3,4,5-tetrahydro[1,3-]diazepino[1,2-a]pyrido[2,3-d]pyrimidine-7(12H)-one.
z-4. 12-(4'-fluorobenzyl)-10-methyl-2,3,4,5-tetrahydro[1,3]diazepino[1,2-a]pyrido[2,3-d]pyrimidine-7(12H)-one.
z-5. 12-cyclopropylmethyl-2,3,4,5-tetrahydro[1,3-]diazepino[1,2-a]purido[2,3-d]pyrimidine-7(12H)-one.
z-6. 12-methyl-2,3,4,5-tetrahydro[1,3]diazepino[1,2-a]pyrido[2,3-d]pyrimidine-7(12H)-one.
z-7. 10-propargyl-2,3-dihydro-imidazo[1,2-a]pyrido[2,3-d]pyrimidine5-(10H)-one.
z-8. 10-(2-butynyl)-2,3-dihydro-imidazo[1,2-a]pyrido[2,3-d]pyrimidine-5(10H)-one.
z-9. 10-cyanomethyl-2,3-dihydro-imidazo[1,2-a]pyrido[2,3-d]pyrimidine-5(10H)-one.

Compounds provided by this application and not disclosed in my prior application Ser. No. 326,850 (now U.S. Pat. No. 3,859,289) are those in which R is alkynyl or cyanoalkyl.

Compounds of the invention of particular interest are also those in which $R_3$ and $R_3'$ are both alkyl with the $R_4$ being hydrogen or alkyl, preferably hydrogen and those in which $R_4$ and $R_4'$ are both alkyl with the $R_3$ being hydrogen or alkyl, preferably hydrogen, and more particularly with n being 0. In such compounds $R_3$, $R_3'$, $R_4$ and $R_4'$ are preferably methyl and/or ethyl, more preferably methyl.

What is claimed is:

1. A compound of the formula:

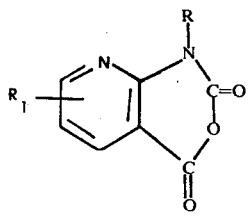

wherein R is alkyl of 1 to 7 carbon atoms, alkenyl of 3 to 8 carbon atoms, alkynyl of 3 to 6 carbon atoms, cyanoalkyl of 2 to 6 carbon atoms,

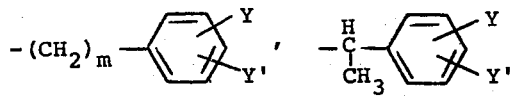

or

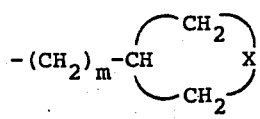

$m$ is 0 to 2,
$R_1$ is hydrogen, alkyl of 1 to 4 carbon atoms or alkoxy of 1 to 3 carbon atoms,
X is a direct bond or $-(CH_2)_p-$,
$p$ is 1 to 3, and
each of Y and Y' is, independently, hydrogen, fluoro, chloro, or lower alkyl of 1 to 3 carbon atoms, or both are lower alkoxy of 1 to 2 carbon atoms, or one is hydrogen and the other bromo, trifluoromethyl, or lower alkoxy of 1 to 2 carbon atoms.

2. A compound of claim 1 in which R is alkyl.
3. A compound of claim 1 in which R is alkenyl.
4. A compound of claim 1 in which R is alkynyl.
5. A compound of claim 1 in which R is cyanoalkyl.
6. A compound of claim 1 in which R is cycloalkyl.
7. A compound of claim 1 in which R is cycloalkylalkyl.
8. A compound of claim 1 in which R is

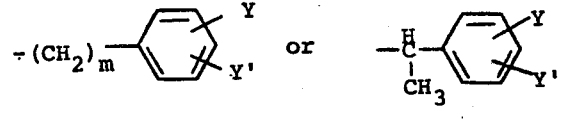

9. A compound of claim 8 in which R is

10. A compound of claim 8 in which R is

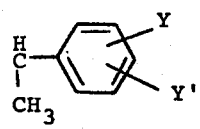

11. A compound of claim 8 in which R is

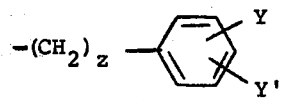

wherein $z$ is 1 or 2.

12. A compound of claim 11 in which $z$ is 1.
13. The compound of claim 12 in which $R_1$ is hydrogen and R is benzyl.
14. The compound of claim 12 in which $R_1$ is hydrogen and R is p-fluorobenzyl.
15. The compound of claim 7 in which $R_1$ is hydrogen and P is cyclopropylmethyl.
16. The compound of claim 6 in which $R_1$ is hydrogen and R is cyclohexyl.
17. A compound of claim 4 in which R is propargyl.
18. A compound of claim 4 in which R is 2-butynyl.
19. A compound of claim 5 in which R is cyanomethyl.
20. The compound of claim 17 in which $R_1$ is hydrogen.
21. The compound of claim 18 in which $R_1$ is hydrogen.
22. A compound of claim 1 in which $R_1$ is hydrogen.

* * * * *